United States Patent
Cafiero et al.

(10) Patent No.: US 10,966,991 B2
(45) Date of Patent: *Apr. 6, 2021

(54) PROCESS FOR PREPARING A DRY POWDER FORMULATION COMPRISING AN ANTICHOLINERGIC, A CORTICOSTEROID AND A BETA-ADRENERGIC

(71) Applicant: CHIESI FARMACEUTICI S.P.A., Parma (IT)

(72) Inventors: Claudio Cafiero, Parma (IT); Leonardo Ortenzi, Parma (IT); Francesca Schiaretti, Parma (IT)

(73) Assignee: CHIESI FARMACEUTICI S.P.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/987,695

(22) Filed: Aug. 7, 2020

(65) Prior Publication Data

US 2020/0368252 A1  Nov. 26, 2020

Related U.S. Application Data

(63) Continuation of application No. 16/113,026, filed on Aug. 27, 2018, now Pat. No. 10,772,896, which is a continuation of application No. 15/351,562, filed on Nov. 15, 2016, now Pat. No. 10,086,004.

(30) Foreign Application Priority Data

Nov. 16, 2015 (EP) ..................................... 15194660

(51) Int. Cl.
| | | |
|---|---|---|
| A61K 31/57 | (2006.01) |
| A61K 47/26 | (2006.01) |
| A61K 9/16 | (2006.01) |
| A61K 31/40 | (2006.01) |
| A61K 47/12 | (2006.01) |
| A61K 45/06 | (2006.01) |
| A61K 31/167 | (2006.01) |
| A61K 9/00 | (2006.01) |
| A61K 31/00 | (2006.01) |
| A61K 9/14 | (2006.01) |
| A61K 31/573 | (2006.01) |

(52) U.S. Cl.
CPC ............ *A61K 31/57* (2013.01); *A61K 9/0075* (2013.01); *A61K 9/145* (2013.01); *A61K 9/1617* (2013.01); *A61K 9/1623* (2013.01); *A61K 31/00* (2013.01); *A61K 31/167* (2013.01); *A61K 31/40* (2013.01); *A61K 31/573* (2013.01); *A61K 45/06* (2013.01); *A61K 47/12* (2013.01); *A61K 47/26* (2013.01)

(58) Field of Classification Search
CPC ...... A61K 31/57; A61K 47/26; A61K 9/1623; A61K 31/40; A61K 47/12; A61K 45/06; A61K 31/167; A61K 9/0075; A61K 9/1617; A61K 31/00; A61K 9/145; A61K 31/573

See application file for complete search history.

(56) References Cited

U.S. PATENT DOCUMENTS

2003/0180227 A1   9/2003 Staniforth et al.

FOREIGN PATENT DOCUMENTS

| WO | 2011/076843 A2 | 6/2011 |
| WO | 2015/004243 A1 | 1/2015 |

OTHER PUBLICATIONS

European search report dated Apr. 14, 2016 issued in corresponding European patent application No. 15194660.5.

*Primary Examiner* — Trevor Love
(74) *Attorney, Agent, or Firm* — Oblon, McClelland, Maier & Neustadt, L.L.P.

(57) ABSTRACT

Dry powder formulations for inhalation containing a combination of an anticholinergic, a long-acting beta$_2$-adrenoceptor agonist, and a corticosteroid are useful for the prevention and/or treatment of an inflammatory and/or obstructive airways disease.

18 Claims, No Drawings

PROCESS FOR PREPARING A DRY POWDER FORMULATION COMPRISING AN ANTICHOLINERGIC, A CORTICOSTEROID AND A BETA-ADRENERGIC

CROSS REFERENCES TO RELATED APPLICATIONS

This application is a continuation of U.S. application Ser. No. 15/351,562, filed on to Nov. 15, 2016, and claims priority to European Patent Application No. 15194660.5, filed on Nov. 16, 2015, which is incorporated herein by reference in its entirety.

BACKGROUND OF THE INVENTION

Field of the Invention

The present invention relates to powder formulations for administration by inhalation by means of a dry powder inhaler. In particular, the present invention relates to processes for preparing a dry powder formulation comprising a combination of an anticholinergic, a beta-adrenoceptor agonist, and an inhaled corticosteroid.

Discussion of the Background

Respiratory diseases are a common and important cause of illness and death around the world. In fact, many people are affected by inflammatory and/or obstructive lung diseases, a category characterized by inflamed and easily collapsible airways, obstruction to airflow, problems exhaling and frequent medical clinic visits and hospitalizations. Types of inflammatory and/or obstructive lung disease include asthma, bronchiectasis, bronchitis and chronic obstructive pulmonary disease (COPD).

In particular, chronic obstructive pulmonary disease (COPD) is a multi-component disease characterized by airflow limitation and airway inflammation. Exacerbations of COPD have a considerable impact on the quality of life, daily activities and general well-being of patients and are a great burden on the health system. Thus, the aim of COPD management includes not only relieving symptoms and preventing disease progression but also preventing and treating exacerbations.

While available therapies improve clinical symptoms and decrease airway inflammation, they do not unequivocally slow long-term progression or address all disease components. With the burden of COPD continuing to increase, research into new and improved treatment strategies to optimize pharmacotherapy is ongoing, and in particular, combination therapies, with a view to their complementary modes of action enabling multiple components of the disease to be addressed. Evidence from recent clinical trials indicates that triple therapy, combining an anticholinergic with an inhaled corticosteroid, and a long-acting $\beta_2$-adrenoceptor agonist, may provide clinical benefits additional to those associated with each treatment alone in patients with more severe COPD.

Currently, there are several recommended classes of therapy for COPD, of which bronchodilators such as β-agonists and anticholinergics are the mainstay of symptom management in mild and moderate diseases, prescribed on an as-needed basis for mild COPD and as a maintenance therapy for moderate COPD.

Said bronchodilators are efficiently administered by inhalation, thus increasing the therapeutic index and reducing side effects of the active material.

For the treatment of more severe COPD, guidelines recommend the addition of inhaled corticosteroids (ICSs) to long-acting bronchodilator therapy. Combinations of therapies have been investigated with a view to their complementary modes of action enabling multiple components of the disease to be addressed. Data from recent clinical trials indicates that triple therapy, combining an anticholinergic with a long-acting $\beta_2$-agonist (LABA), and an ICS, may provide clinical benefits additional to those associated with each treatment alone in patients with moderate to severe forms of respiratory diseases, particular moderate to severe COPD.

An interesting triple combination, presently under investigation, includes:
  i) formoterol, particularly its fumarate salt (hereinafter indicated as FF), a long acting beta-2 adrenergic receptor agonist, currently used clinically in the treatment of asthma, COPD and related disorders;
  ii) glycopyrronium bromide, an anticholinergic (antimuscarinic) recently approved for the maintenance treatment of COPD; and
  iii) beclometasone dipropionate (BDP) a potent anti-inflammatory corticosteroid, available under a wide number of brands for the prophylaxis and/or treatment of asthma and other respiratory disorders.

The solution formulation for administration by pressurized metered dose inhalers (pMDI) is disclosed in WO 2011/076843, which is incorporated herein by reference in its entirety.

Said formulation provides a high lung deposition and uniform distribution throughout the bronchial tree, and is characterized by the fact that is capable of delivering a high fraction of particles having a diameter equal or less than 2.0 micron for all the three active ingredients (hereinafter defined as extrafine fraction).

The major advantage of said formulation is related to the improved penetration into the bronchiole-alveolar distal part of the respiratory tree wherein inflammation is known to play a role in spontaneous exacerbations of asthma symptoms and wherein it is known that the density of the beta-2 adrenergic receptors is particularly high.

However, despite their popularity, pMDI formulations may have some disadvantages in particular in elderly and pediatric patients, mostly due to their difficulty to synchronize actuation from the device with inspiration.

Dry powder inhalers (DPIs) constitute a valid alternative to MDIs for the administration of drugs to airways.

On the other hand, drugs intended for inhalation as dry powders should be used in the form of micronized particles. Their volumetric contribution could represent an obstacle to the design of a formulation therapeutically equivalent to one wherein the drugs are delivered inform of liquid droplets.

Powder formulations for inhalation containing all said three active ingredients in a fixed combination are disclosed in WO 2015/004243, which is incorporated herein by reference in its entirety. Said formulation takes advantage of the technology platform disclosed in WO 01/78693, which is incorporated herein by reference in its entirety, entailing the use of carrier constituted of a fraction of coarse excipient particles and a fraction made of fine excipient particles and magnesium stearate.

In particular the teaching of WO 2015/044243, which is incorporated herein by reference in its entirety, is mainly focused at providing an "extrafine" powder formulation wherein all the active ingredients have very small particle size to deeply reach the distal tract of the respiratory tree.

On the other hand, the aforementioned formulation has been tailored for administration with NEXThaler, a dry powder inhaler specifically designed to generate extrafine particles, and hence being particularly efficient (see Corradi M et al Expert Opin Drug Deliv 2014, 11(9), 1497-1506, which is incorporated herein by reference in its entirety).

Accordingly, the formulation of WO 2015/004243, which is incorporated herein by reference in its entirety, loaded in highly performing dry powder inhaler may turn out to be too efficient to match the performances of the corresponding pMDI formulation in form of solution, and hence its therapeutic characteristics.

Thus, there remains a need for powder formulations suitable for highly performing dry powder inhalers (DPIs) comprising formoterol fumarate, glycopyrronium bromide, and BDP in combination, overcoming the problems indicated above and in particular to provide a powder formulation having therapeutic characteristics matching those of the corresponding pMDI formulation in form of solution.

SUMMARY OF THE INVENTION

Accordingly, it is one object of the present invention to provide novel powder formulations suitable for highly performing dry powder inhalers (DPIs) comprising formoterol fumarate, glycopyrronium bromide, and BDP in combination.

It is another object of the present invention to provide novel powder formulations suitable for highly performing dry powder inhalers (DPIs) comprising formoterol fumarate, glycopyrronium bromide, and BDP in combination, overcoming the problems indicated above and in particular to provide a powder formulation having therapeutic characteristics matching those of the corresponding pMDI formulation in form of solution.

It is another object of the present invention to provide novel methods of preparing such a formulation.

It is another object of the present invention to provide novel methods of preventing and/or treating a disease of the respiratory tract by administering such a formulation.

These and other objects, which will become apparent during the following detailed description, have been achieved by the inventors' discovery of a process for preparing a powder formulation for inhalation for use in a dry powder inhaler, said powder comprising:

(A) a carrier, comprising:
(a) 80 to 95 percent by weight, based on the total weight of said carrier, of coarse particles of a physiologically acceptable excipient having a mean particle size of at least 175 μm; and
(b) 19.6 to 4.9 percent by weight, based on the total weight of said carrier, of micronized particles of a physiologically acceptable excipient, and 0.1 to 0.4 percent by weight, based on the total weight of said carrier, of a salt of a fatty acid; and
(B) micronized particles of an anti-muscarinic drug, a long-acting $\beta_2$-agonist (LABA), and optionally, an inhaled corticosteroid (ICS), as active ingredients, said process comprising:
(i) mixing all of said coarse particles of a physiologically acceptable excipient, all of said salt of a fatty acid, a first portion of said micronized particles of a physiologically acceptable excipient, all of said micronized particles of said long-acting $\beta_2$-agonist, said anti-muscarinic drug, and, optionally, said inhaled corticosteroid in a vessel of a shaker mixer at a speed of rotation not lower than 16 r.p.m. for a time of not less than 60 minutes, to obtain a first mixture; and (ii) adding the remaining part of said micronized particles of a physiologically acceptable excipient to said first mixture, to obtain a second mixture, and mixing said second mixture at a speed of rotation not lower than 16 rpm for a time of at least 120 minutes.

In a preferred embodiment, the anti-muscarinic drug is glycopyrronium bromide, the ICS is beclometasone dipropionate, the LABA is formoterol fumarate dihydrate, and the additive is magnesium stearate.

Therefore, in a second aspect, the present invention is directed to a powder formulation for inhalation for use in a dry powder inhaler, said powder comprising:

(A) a carrier, comprising:
(a) 80 to 95 percent by weight, based on the total weight of said carrier, of coarse particles of a physiologically acceptable excipient having a mean particle size of at least 175 μm; and
(b) 19.6 to 4.9 percent by weight, based on the total weight of said carrier, of micronized particles of a physiologically acceptable excipient, and 0.1 to 0.4 percent by weight, based on the total weight of said carrier, of magnesium stearate; and
(B) micronized particles of glycopyrronium bromide, beclometasone dipropionate, and formoterol fumarate dihydrate, as active ingredients, wherein said formulation is obtainable by a process comprising:
(i) mixing all of said coarse particles of a physiologically acceptable excipient, all of said magnesium stearate, a first portion of said micronized particles of a physiologically acceptable excipient, all of said micronized particles of glycopyrronium bromide, beclometasone dipropionate, and formoterol fumarate dihydrate in a vessel of a shaker mixer at a speed of rotation not lower than 16 rpm for a time of not less than 60 minutes, to obtain a first mixture; and (ii) adding the remaining part of said micronized particles of a physiologically acceptable excipient to said first mixture, to obtain a second mixture, and mixing said second mixture at a speed of rotation not lower than 16 for a time of at least 120 minutes; whereby the extrafine particle fraction of each active ingredient is comprised between 20 and 35%.

In a third aspect, the present invention concerns a dry powder inhaler device filled with the above dry powder formulations. Preferably the dry powder inhaler is a high-performing dry powder inhaler.

In a fourth aspect, the present invention refers to the claimed formulations for use in the prevention and/or treatment of an inflammatory and/or obstructive airways disease, in particular asthma or chronic obstructive pulmonary disease (COPD).

In a fifth aspect, the present invention provides a method for the prevention and/or treatment of an inflammatory and/or obstructive airways disease, in particular asthma or chronic obstructive pulmonary disease (COPD), comprising administering by inhalation, to a subject in need thereof, an effective amount of the formulations of the present invention.

In a sixth aspect, the present invention refers to the use of the claimed formulations in the manufacture of a medicament for the prevention and/or treatment of an inflammatory and/or obstructive airways disease, in particular asthma or chronic obstructive pulmonary disease (COPD).

DETAILED DESCRIPTION OF THE PREFERRED EMBODIMENTS

As used herein, the term "dry powder inhaler (DPI)" refers to a device that delivers medication to the lungs in the form of a dry powder DPIs can be divided into two basic types:

i) single dose inhalers, for the administration of pre-subdivided single doses of the active compound;

ii) multidose dry powder inhalers (MDPIs), either with pre-subdivided single doses or pre-loaded with quantities of active ingredient sufficient for multiple doses; each dose is created by a metering unit within the inhaler.

On the basis of the required inspiratory flow rates (l/min) which in turn are strictly depending on their design and mechanical features, DPI's are also divided in:

i) low-resistance devices (>90 l/min);
ii) medium-resistance devices (about 60-90 l/min);
iii) medium-high resistance devices (about 50-60 l/min);
iv) high-resistance devices (less than 30 l/min).

The reported classification is generated with respect to the flow rates required to produce a pressure drop of 4 KPa (KiloPascal) in accordance to the European Pharmacopoeia (Eur Ph), which is incorporated herein by reference in its entirety.

As used herein, the term "high-performing dry powder inhaler (DPI)" refers to a medium or high resistance breath-actuated multidose dry powder inhaler having a body with a mouthpiece and provided with a deagglomerator system for deagglomerating the powdered medicament comprising a vortex chamber (cyclone), wherein the air flow for the delivery of the medicament is not lower than 20 l/min, preferably in the range 25 to 40 l/min.

The term is "muscarinic receptor antagonists", "anti-muscarinic drugs" and "anticholinergic drugs" can be used synonymously.

The term "pharmaceutically acceptable salt of glycopyrrolate" refers to a salt of the compound (3S,2'R), (3R,2'S)-3-[(cyclopentylhydroxyphenylacetyl)oxy]-1,1-dimethylpyrrolidinium in approximately 1:1 racemic mixture, also known as glycopyrronium salt.

The term "pharmaceutically acceptable salt of formoterol" refers to a salt of the compound 2'-hydroxy-5'-5-[(RS)-1-hydroxy-2 {[(RS)-p-methoxy-α-methylphenethyl]amino}ethyl] formanilide.

The term "beclometasone dipropionate" refers to the compound (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[α]phenanthren-17-yl propionate.

The term "pharmaceutically acceptable salt" comprises inorganic and organic salts. Examples of organic salts may include formate, acetate, trifluoroacetate, propionate, butyrate, lactate, citrate, tartrate, malate, maleate, succinate, methanesulfonate, benzenesulfonate, xinafoate, pamoate, and benzoate. Examples of inorganic salts may include fluoride chloride, bromide, iodide, phosphate, nitrate and sulphate.

The term "physiologically acceptable excipient" refers to a pharmacologically-inert substance to be used as a carrier. In the context of the present invention, salts of fatty acids, that are also physiologically acceptable excipients, are defined as an additive.

The expression "shaker mixer" refers to a versatile mixer having a wide and adjustable range of speed of rotation and inversion cycles. In said mixers, the mixing container is gimbal-mounted. Two rotation axes are positioned perpendicularly each other, and are powered independently. The turning direction and rotational speed of both axes is subject to continual and independent change. The setting of these kind of mixing process parameters is able to guarantee an high value of mixing efficiency. A typical shaker mixer is commercially available as dyna-MIX™ (Willy A. Bachofen A G, Switzerland) or 3D.S mixer (Erhard Muhr GmbH, Germany).

The expression "tumbler mixer" refers to a mixer that works with different mixing times and mixing speeds and but with a typical movement characterized by the interaction of rotation, translation and inversion. A typical tumbler mixer is commercially available as Turbula™ (Willy A Bachofen AG. Switzerland).

The expression instant or high-shear mixer refers to mixers wherein a rotor or impeller, together with a stationary component known as a stator is used either in a tank containing the powder to be mixed to create a shear.

Typical high-shear mixers are P 100 and P 300 (Diosna GmbH, Germany), Roto Mix (IMA, Italy), and Cyclomix™ (Hosokawa Micron Group Ltd, Japan).

The term "micronized" refers to a substance having a size of few microns.

The term "coarse" refers to a substance having a size of one or few hundred microns.

In general terms, the particle size of particles is quantified by measuring a characteristic equivalent sphere diameter, known as volume diameter, by laser diffraction.

The particle size can also be quantified by measuring the mass diameter by means of suitable known instrument such as, for instance, the sieve analyzer.

The volume diameter (VD) is related to the mass diameter (MD) by the density of the particles (assuming a size independent density for the particles).

In the present application, the particle size of the active ingredients and of fraction of fine particles is expressed in terms of volume diameter, while that of the coarse particles is expressed in terms of mass diameter.

The particles have a normal (Gaussian) distribution which is defined in terms of the volume or mass median diameter (VMD or MMD) which corresponds to the volume or mass diameter of 50 percent by weight of the particles, and, optionally, in terms of volume or mass diameter of 10% and 90% of the particles, respectively.

Another common approach to define the particle size distribution is to cite three values:

i) the median diameter d(0.5) which is the diameter where 50% of the distribution is above and 50% is below;

ii) d(0.9), where 90% of the distribution is below this value; and iii) d(0.1), where 10% of the distribution is below this value.

The span is the width of the distribution based on the 10%, 50% and 90% quantile and is calculated according to the formula.

$$\mathrm{Span} = \frac{D[v, 0.9] - D[v, 0.1]}{D[v, 0.5]}$$

In general terms, particles having the same or a similar VMD or MMD can have a different particle size distribution, and in particular a different width of the Gaussian distribution as represented by the d(0.1) and d(0.9) values.

Upon aerosolization, the particle size is expressed as mass aerodynamic diameter (MAD), while the particle size distribution is expressed in terms of Mass median aerodynamic diameter (MMAD) and Geometric Standard Deviation (GSD). The MAD indicates the capability of the particles of being transported suspended in an air stream. The MMAD corresponds to the mass aerodynamic diameter of 50 percent by weight of the particles.

In the final formulation the particle size of the active ingredients can be determined by scanning electron microscopy according to methods known to the skilled person in the art.

The term "hard pellets" refers to spherical or semispherical units whose core is made of coarse excipient particles.

The term "spheronization" refers to the process of rounding off of the particles which occurs during the treatment.

The term "good flowability" refers to a formulation that is easy handled during the manufacturing process and is able of ensuring an accurate and reproducible delivery of the therapeutically effective dose.

Flow characteristics can be evaluated by different tests such as angle of repose, Carr's index, Hausner ratio or flow rate through an orifice.

In the context of the present application the flow properties were tested by measuring the flow rate through an orifice according to the method described in the European Pharmacopeia (Eur. Ph.) 8.6, $8^{th}$ Edition, which is incorporated herein by reference in its entirety.

The expression "good homogeneity" refers to a powder wherein, upon mixing, the uniformity of distribution of a component, expressed as coefficient of variation (CV) also known as relative standard deviation (RSD), is less than 5.0%. It is usually determined according to known methods, for instance by taking samples from different parts of the powder and testing the component by HPLC or other equivalent analytical methods.

The expression "respirable fraction" refers to an index of the percentage of active particles which would reach the lungs in a patient.

The respirable fraction is evaluated using a suitable in viro apparatus such as Andersen Cascade Impactor (ACI), Multi Stage Liquid Impinger (MLSI) or Next Generation Impactor (NGI), according to procedures reported in common Pharmacopoeias, in particular in the European Pharmacopeia (Eur. Ph.) 8.4, $8^{th}$ Edition, which is incorporated herein by reference in its entirety.

It is calculated by the percentage ratio of the fine particle mass (formerly fine particle dose) to the delivered dose.

The delivered dose is calculated from the cumulative deposition in the apparatus, while the fine particle mass is calculated from the deposition of particles having a diameter <5.0 micron.

In the context of the present invention, the formulation is defined as extrafine formulation when, upon inhalation, the active ingredients are delivered with a fraction of particles having a particle size equal to or lower than 2.0 micron equal to or higher than 20%.

With the term "mid FPF" is defined as the fraction of delivered dose having a particle size comprised between 0.2.0 and 5.0 micron.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al. J. Pharm. Pharmacol. 34, 700-706, 1982, which is incorporated herein by reference inits entirety, and it is considered acceptable if the distribution of the active ingredient in the powder formulation after the test, expressed as relative standard deviation (RSD), does not change significantly with respect to that of the formulation before the test.

The expression "chemically stable" refers to a formulation that, upon storage, meets the requirements of the EMEA Guideline CPMP/QWP/122/02, which is incorporated herein by reference in its entirety, referring to 'Stability Testing of Existing Active Substances and Related Finished Products'.

The term "surface coating" refers to the covering of the surface of the carrier particles by forming a film of magnesium stearate around said particles. The thickness of the film has been estimated by X-ray photoelectron spectroscopy (XPS) to be approximately of less than 10 nm. The percentage of surface coating indicates the extent by which magnesium stearate coats the surface of all the carrier particles.

The term "prevention" means an approach for reducing the risk of onset of a disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. The term can also mean prolonging survival as compared to expected survival if not receiving treatment.

According to the Global Initiative for Asthma (GINA), which is incorporated herein by reference in its entirety, "uncontrolled persistent asthma" is defined as a form characterized by daily symptoms, frequent exacerbations, frequent nocturnal asthma symptoms, limitation of physical activities, forced expiratory volume in one second ($FEV_1$) equal to or less than 80% predicted and with a variability higher than 30%. According to the Global Initiative for Asthma (GINA) guidelines 2014, which is incorporated herein by reference in its entirety, "partially uncontrolled asthma" is defined as a form characterized by less than twice a week daily symptoms, less than twice a month, nocturnal asthma symptoms, and a forced expiratory volume in one second ($FEV_1$) higher than 80% with a variability comprised between 20 and 30%.

According to the Global initiative for chronic Obstructive Pulmonary Disease (GOLD) guidelines which is incorporated herein by reference in its entirety, "severe COPD" is a form characterized by a ratio between $FEV_1$ and the Forced Vital Capacity (FVC) lower than 7 and $FEV_1$ between 30% and 50% predicted. The very severe form is further characterized by chronic respiratory failure.

"Therapeutically effective dose" means the quantity of active ingredients administered at one time by inhalation upon actuation of the inhaler. Said dose may be delivered in one or more actuations, preferably one actuation (shot) of the inhaler. The term "actuation" refers to the release of active ingredients from the device by a single activation (e.g. mechanical or breath).

Wherein a numerical range is stated herein, the endpoints are included.

The present invention is directed to a process for the preparation of a dry powder formulation for use in a dry powder inhaler (DPI) comprising a carrier, and micronized particles of an anticholinergic, a long-acting $\beta_2$-agonist (LABA), and, optionally, an inhaled corticosteroid (ICS), as active ingredients.

The LABA active ingredient, that may be present in form of pharmaceutically acceptable salts and/or solvate form thereof, can be selected from a group, which include, but it is not limited to, formoterol, salmeterol, indacaterol, olodaterol, vilanterol, and the ultra-long-acting β2-adrenoreceptor agonist (uLABA) compound quoted with the code AZD3199.

The anticholinergic, that is usually present in form of pharmaceutically acceptable inorganic salts, can be selected from a group which include, but it is not limited to, glycopyrronium bromide or chloride, tiotropium bromide, umeclidinium bromide, aclidinium bromide, and the compound quoted with the code GSK 233705.

The ICS, that may be anhydrous or present in form of hydrates, can be selected from a group which include, but it is not limited to, beclomethasone dipropionate and its monohydrate form, budesonide, fluticasone propionate, fluticasone furoate, and mometasone furoate.

Preferably, the LABA is formoterol fumarate dihydrate, the ICS is beclometasone dipropionate, and the anticholinergic is glycopyrronium bromide.

The carrier A) is constituted of a) a fraction of coarse excipient particles and a fraction b) constituted of micronized excipients particles, and a salt of a fatty acid as an additive contributing to improve the respirable fraction.

The coarse excipient particles consist of 80 to 95 percent by weight of particles of a physiologically acceptable excipient having a mass median diameter equal to or higher 175 micron.

Advantageously, all the coarse particles have a mass diameter in the range comprised between 100 and 600 micron.

In certain embodiments of the invention, the mass diameter of said coarse particles might be between 150 and 500 micron, preferably between 200 and 400 micron.

In a preferred embodiment of the invention, the mass diameter of the coarse particles is comprised between 210 and 360 micron.

In general, the skilled person shall select the most appropriate size of the coarse excipient particles if commercially available or by sieving, using a proper classifier.

Advantageously, the coarse excipient particles may have a relatively highly fissured surface, that is, on which there are clefts and valleys and other recessed regions, referred to herein collectively as fissures. The "relatively highly fissured" coarse particles can be defined in terms of fissure index and/or rugosity coefficient as described in WO 01/78695 and WO 01/78693, which are incorporated herein by reference in their entireties, and they could be characterized according to the description therein reported. Advantageously, the fissure index of said coarse particles is of at least 1.25, preferably of at least 1.5, more preferably of at least 2.0.

Said coarse particles may also be characterized in terms of tapped density or total intrusion volume measured as reported in WO 01/78695, which is incorporated herein by reference in its entirety.

The tapped density of said coarse particles could advantageously be less than 0.8 g/cm$^3$, preferably 0.8 to 0.5 g/cm$^3$. The total intrusion volume could be of at least 0.8 cm$^3$, preferably at least 0.9 cm$^3$.

The fraction of micronized particles b) comprises of 19.6 to 4.9 percent by weight of particles of a physiologically acceptable excipient wherein at least 90% of said particles have a volume diameter lower than 15 micron, preferably lower than 12 micron. Advantageously, the volume median diameter of said particles is 3 to 7 micron, preferably 4 to 6 micron and no more than 10% of said particles have a diameter lower than 2.5 micron, preferably lower than 2.0 micron.

Advantageously, the fine and coarse excipient particles may consist of any pharmacologically inert, physiologically acceptable material or combination thereof; preferred excipients are those made of crystalline sugars, in particular lactose; the most preferred are those made of α-lactose monohydrate.

Preferably, the coarse excipient particles and the fine excipient particles both consist of α-lactose monohydrate.

Said fraction b) further comprises 0.1 to 0.4 percent by weight of a salt of fatty acids such as lauric acid, palmitic acid, stearic acid, behenic acid, or derivatives (such as esters and salts) thereof. Specific examples of such salts of fatty acids are: magnesium stearate; sodium stearyl fumarate; sodium stearyl lactylate; sodium lauryl sulphate, magnesium lauryl sulphate.

The preferred salt of fatty acid is magnesium stearate.

Advantageously, if it is used as the additive, magnesium stearate coats the surface of the coarse and micronized excipient particles a) and b) in such a way that the extent of the surface coating is at least of 5% more advantageously, higher than 10%.

The extent to which the magnesium stearate coats the surface of the excipient particles may be determined by X-ray photoelectron spectroscopy (XPS), a well-known tool for determining the extent as well as the uniformity of distribution of certain elements on the surface of other substances. In the XPS instrument, photons of a specific energy are used to excite the electronic states of atoms below the surface of the sample, Electrons ejected from the surface are energy filtered via a hemispherical analyser (HSA) before the intensity for a defined energy is recorded by a detector. Since core level electrons in solid-state atoms are quantized, the resulting energy spectra exhibit resonance peaks characteristic of the electronic structure for atoms at the sample surface.

Typically XPS measurements are taken on an Axis-Ultra instrument available from Kratos Analytical (Manchester, UK) using monochromated Al Kα radiation. (1486.6 eV) operated at 15 mA emission current and 10 kV anode potential (150 W). A low energy electron flood gun is used to compensate for insulator charging. Survey scans, from which quantification of the detected elements are obtained, are acquired with analyser pass energy of 160 eV and a 1 eV step size. High-resolution scans of the C 1s, O 1s, Mg 2s, N 1s and Cl 2p regions are acquired with pass energy of 40 eV and a 0.1 eV step size. The area examined is approximately 700 μm×300 m for the survey scans and a 110 μm diameter spot for the high-resolution scans.

In the context of the present invention, it is possible to calculate by XPS both the extent of coating and the depth of the magnesium sterate film around the lactose particles. The extent of magnesium stearate (MgSt) coating is estimated using the following equation:

% MgSt coating=(% Mg$_{sample}$/% Mg$_{ref}$)×100 where:

Mg$_{sample}$ is the amount of Mg in the analyzed mixture; and

Mg$_{ref}$ is the amount of Mg in the reference sample of commercially available MgSt.

Usually the values are calculated as a mean of two different measurements. Typically, an accuracy of 10% is quoted for routinely performed XPS experiments.

Alternatively, when the excipient particles are made of lactose, preferably of alpha-lactose monohydrate, the extent of surface coating may be determined by water contact angle measurement, and then by applying the equation known in the literature as Cassie and Baxter, for example cited at page 338 of Colombo I et a II Farmaco 1984, 39(10), 328-341, which is incorporated herein by reference in its entirety, and reported below.

$$\cos \vartheta_{mixture} = f_{MgSt} \cos \vartheta MgSt + f_{lactose} \cos \vartheta_{lactose}$$

where:

$f_{MgSt}$ and $f_{lactose}$ are the surface area fractions of magnesium stearate and of lactose;

$\vartheta_{MgSt}$ is the water contact angle of magnesium stearate;

$\vartheta_{lactose}$ is the water contact angle of lactose; and $\vartheta_{mixture}$ it are the experimental contact angle values.

For the purpose of the present invention, the contact angle may be determined with methods that are essentially based on a goniometric measurement. These imply the direct observation of the angle formed between the solid substrate and the liquid under testing. It is therefore quite simple to carry out, being the only limitation related to possible bias stemming from intra-operator variability. It should be however underlined that this drawback can be overcome by adoption of a fully automated procedure, such as a computer assisted image analysis, A particularly useful approach is the sessile or static drop method which is typically carried out by depositing a liquid drop onto the surface of the powder in form of disc obtained by compaction (compressed powder disc method).

Within the limits of the experimental error, a good consistency has been found between the values of extent of coating as determined by XPS measurements, and those as estimated by the theoretical calculations based on the Cassie and Baxter equation.

The extent to which the magnesium stearate coats the surface of the excipient particles may also be determined by scanning electron microscopy (SEM), a well-known versatile analytical technique.

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of the excipient particles.

SEM may alternatively be combined with IR or Raman spectroscopy for determining the extent of coating, according to known procedures.

More advantageously, the ratio among the fraction of coarse particles a), the micronized excipient particles, and magnesium stearate shall be comprised between 85:14.7:0.3 and 90:9.8:0.2 by weight, preferably 90:9.8:0.2 by weight.

Advantageously, the whole amount of coarse particles a) are mixed with the whole amount of magnesium stearate and with a first portion of the micronized excipient particles.

Advantageously, said first portion is 40% to 60%, more advantageously 45 to 55%, preferably 50%, based on the total weight of all micronized excipient particles.

The mixing may be performed in any suitable mixer, e.g. tumbler mixers such as Turbular™ for at least 5 minutes, preferably for at least 30 minutes, more preferably for at least two hours.

In a general way, the skilled person shall adjust the time of mixing and the speed of rotation of the mixer to obtain a homogenous mixture.

When spheronized coarse excipient particles are desired to obtain hard-pellets according to the definition reported above, the step of mixing shall be typically carried out for at least four hours.

Since the mixing step does not alter the particle size, the person skilled in the art shall select the suitable size of the coarse excipient particles, that of the micronized excipient particles as well as that of magnesium stearate, either by sieving, by using a classifier to achieve the desired particle size distribution, being sure that final particle size of blend will correspond to the staring one.

Materials of the desired particle size distribution are also commercially available.

In one embodiment of the invention, the carrier A consisting of the coarse excipient particles a), 50% of the micronized excipient particles and the particles of magnesium stearate may be prepared by mixing in a Turbula™ mixer or in a dyna-MLX mixer at a rotation speed of 11 to 45 rpm preferably 16 to 32 rpm, for a period of at least 30 minutes, preferably comprised between 60 and 300 minutes.

In step i), the carrier A), the micronized particles of the ICS, the LABA and the anti-muscarinic drug are poured in the vessel of a shaker mixer having a wide and adjustable range of speed of rotation and inversion cycles.

It has indeed been found that said type of mixers is particularly suitable due to their versatility. In fact, with said mixers, frequent changes in the revolution cycles can be set in order to continuously change the powder flow inside the mixing and create powder flow patterns within the drum and to increase mixing efficacy.

In a preferred embodiment of the invention, the dyna-MIX™ mixer is utilized.

The blend of step i) is mixed at a speed of rotation of at least 16 r.p.m., preferably between 20 and 28 r.p.m, for a time of not less than 60 minutes, preferably comprised between 60 and 120 minutes.

In step ii), the remaining part of the micronized physiologically acceptable excipient is added and mixed at a speed of rotation not lower than 16 rpm, preferably between 16 and 32 r.p.m., or a time of at least 120 minutes, preferably between 120 and 180 minutes.

Contrary to what reported in the prior an it has indeed been found that by adding micronized, and hence fine, particles of the excipient after the mixing of the active ingredients with the carrier, it is possible to reduce the de-aggregation of said active ingredients, and hence decrease the respirable fraction.

Without being limited by the theory, this might be due that the micronized excipient particles cover the active ingredients particles, so partly preventing their de-aggregation.

Moreover, by proper controlling the amount of the micronized excipient particles, it could be possible the extent of the reduction of the respirable fraction.

Optionally, the resulting mixture is sieved through a sieve. The skilled person shall select the mesh size of the sieve depending on the particle size of the coarse particles.

The blend of step ii) is finally mixed in any suitable mixer to achieve an homogeneous distribution of the active ingredients.

The skilled person shall select the suitable mixer and adjust the time of mixing and the speed of rotation of the mixer to obtain a homogenous mixture.

Advantageously, each active ingredient is present in the formulation of the invention in a crystalline form, more preferably with a crystallinity degree higher than 95%, even more preferably higher than 98%, as determined according to known methods.

Since the powder formulation obtained with the process of the invention should be administered to the lungs by inhalation, at least 99% of said particles (d(v,0.99)) shall have a volume diameter equal to or lower than 10 micron, and substantially all the particles have a volume diameter comprised between 8 and 0.4 micron.

Advantageously, in order to better achieve the distal tract of the respiratory tree, 90% of the micronized particles of the ICS and LABA active ingredients shall have a volume diameter lower than 6.0 micron, preferably equal to or lower than 5.0 micron, the volume median diameter shall be comprised between 1.2 and 2.5 micron, preferably between 0.3 and 2.2 micron, and no more than 10% of said shall have a diameter lower than 0.6 micron, preferably equal to or lower than 0.7 micron, more preferably equal to or lower than 0.8 micron.

It follows that the width of the particle size distribution of the particles of the ISC and LABA active ingredients, expressed as a span, shall be advantageously comprised between 1.0 and 4,0, more advantageously between 1.2 and 3.5 According the Chew et al *J Pharm Pharmaceut Sci* 2002, 5, 162-168, which is incorporated herein by reference in its entirety, the span corresponds to [d (v, 0.9)–d(v,0.1)]/d(v, 0.5).

In the case of the anticholinergic drug, in order to achieve both the distal and upper tract of the respiratory tree, 90% of the micronized particles shall have a volume diameter equal to or lower than 8.0 micron, preferably equal to or lower than 7.0 micron, the volume median diameter shall be comprised between 1.2 and 4.0 micron, preferably between 1.7 and 3.5 micron, and no more than 10% of said have a diameter lower than 0.5 micron, preferably equal to or lower than 0.6 micron, more preferably equal to or lower than 0.8 micron.

It follows that the width of the particle size distribution of the particles of the anticholinergic drug, expressed as a span, shall be advantageously comprised between 0.1.0 and 5.0, more advantageously between 1.2 and 4.0.

The size of the particles of the active ingredients is determined by measuring the characteristic equivalent sphere diameter, known as volume diameter, by laser diffraction. In the reported examples, the volume diameter has been determined using a Malvern apparatus. However, other equivalent apparatus may be used by the skilled person in the art.

In a preferred embodiment, the Helos Aspiros instrument (Sympatec GmbH, Clausthal-Zellerfeld, Germany) is utilized. Typical conditions are: Fraunhofer FREE or Fraunhofer HRLD algorithm, R1 (0.1/0.18-35 micron) or R2 (0.25/0.45-87.5 micron) lens, 1 bar pressure.

As for the particle size determination, a CV of ±30% for the d(v0,1) and a CV of ±20% for the d(v0,5), d(v0,9) and d(v0,99) are considered within the experimental error.

In a preferred embodiment of the invention, the LABA is formoterol fumarate dihydrate, the ICS is beclometasone dipropionate, the anticholinergic is glycopyrronium bromide, and the additive is magnesium stearate.

Accordingly, in a particularly embodiment, the invention is directed to a powder formulation for inhalation for use in a dry powder inhaler, said powder comprising:

(A) a carrier, comprising:
(a) 80 to 95 percent by weight, based on the total weight of said carrier, of coarse particles of a physiologically acceptable excipient having a mean particle size of at least 175 μm; and
(b) 196 to 4.9 percent by weight, based on the total weight of said carrier, of micronized particles of a physiologically acceptable excipient, and 0.1 to 0.4 percent by weight, based on the total weight of said carrier, of magnesium stearate; and
(B) micronized particles of glycopyrronium bromide, beclometasone dipropionate, and formoterol fumarate dihydrate, as active ingredients,
wherein said formulation is obtainable by a process comprising:
(i) mixing all of said coarse particles of a physiologically acceptable excipient, all of said magnesium stearate, a first portion of said micronized particles of a physiologically acceptable excipient, all of said micronized particles of glycopyrronium bromide, beclometasone dipropionate, and formoterol fumarate dihydrate in a vessel of a shaker mixer at a speed of rotation not lower than 16 rpm for a time of not less than 60 minutes, to obtain a first mixture; and
(ii) adding the remaining part of said micronized particles of a physiologically acceptable excipient to said first mixture, to obtain a second mixture, and mixing said second mixture at a speed of rotation not lower than 16 rpm for a time of at least 120 minutes;
whereby the extrafine particle fraction of each active ingredient is comprised between 20 and 35%.

In a preferred embodiment, the extrafine particle fraction of beclometasone dipropionate, and formoterol fumarate dihydrate is comprised between 20 and 35%, and the extrafine particle fraction of glycopyrronium bromide is comprised between 20 and 30%.

Advantageously, in order to better achieve the distal tract of the respiratory tree, 90% of the micronized particles of beclometasone dipropionate (BDP), and formoterol fumarate dihydrate shall have a volume diameter lower than 6.0 micron, preferably equal to or lower than 5.0 micron, the volume median diameter shall be comprised between 1.2 and 2.5 micron, preferably between 1.3 and 2.2 micron, and no more than 10% of said shall have a diameter lower than 0.6 micron, preferably equal to or lower than 0.7 micron, more preferably equal to or lower than 0.8 micron.

It follows that the width of the particle size distribution of the particles of the BDP and formoterol fumarate dihydrate, expressed as a span, shall be advantageously comprised between 1.0 and 4.0, more advantageously between 1.2 and 3.5.

In the case of glycopyrronium bromide, in order to achieve both the distal and upper tract of the respiratory tree, 90% of the micronized particles shall have a volume diameter equal to or lower than 8.0 micron, preferably equal to or lower than 7.0 micron, the volume median diameter shall be comprised between 1,2 and 4.0 micron, preferably between 1.7 and 3.5 micron, and no more than 10% of said have a diameter lower than 0.5 micron, preferably equal to or lower than 0.8 micron, more preferably equal to or lower than 1.0 micron.

It follows that the width of the particle size distribution of the particles of the anticholinergic drug, expressed as a span, shall be advantageously comprised between 1.0 and 5.0, more advantageously between 1.2 and 4.0.

More advantageously, it would also be preferable that the micronized particles of BDP have a Specific Surface Area comprised between 5.5 and 7.0 m$^2$/g, preferably between 5.9 and 6.8 m²/g, the micronized particles of formoterol fumarate dihydrate have a Specific Surface Area comprised between 5 and 7.5 mg, preferably between 5,2. and 6.5 m²/g, more preferably between 5.5 and 5.8 m²/g, and the micronized particles of glycopyrronium bromide have a Specific Surface Area comprised between 1.8 and 5.0 m²/g preferably between 2.0 and 4.5 m²/g.

The Specific Surface Area is determined by Brunauer-Emmett-Teller (BET) nitrogen adsorption method according to a known procedure known.

All the micronized active ingredients utilized in the formulation according to the present invention may be prepared by processing in a suitable mill according to known methods.

In one embodiment of the present invention, they could be prepared by grinding using a conventional fluid energy mill such as commercially available jet mill micronizers having grinding chambers of different diameters.

Depending on the type of the apparatus and size of the batch, the person skilled in the art shall suitably adjust the milling parameters such as the operating pressure, the feeding rate and other operating conditions to achieve the desired particle size. Preferably all the micronized active ingredients are obtained without using any additive during the micronization process.

In another embodiment of the present invention, the micronized particles of glycopyrronium bromide may be prepared according to the process disclosed in WO 2014/73987, which is incorporated herewith by reference in its entirety.

The powder formulation comprising micronized particles of glycopyrronium bromide, beclometasone dipropionate, and formoterol fumarate dihydrate as active ingredients obtainable according to process of the present invention is physically and chemically stable, freely flowable and exhibits a good homogeneity of the active ingredients.

Moreover, the above powder formulation delivered through a high-performing DPI such as that disclosed in WO 2004/012801, which is incorporated herein by reference in its entirety, turned out to therapeutically equivalent to the corresponding pMDI formulation in solution.

The ratio between the carrier particles and the active ingredients will depend on the type of inhaler used and the required dose.

The powder formulations of the present invention may be suitable for delivering a therapeutic amount of all active ingredients in one or more actuations (shots or puffs) of the inhaler.

Advantageously, the formulations of the present invention shall be suitable for delivering a therapeutically effective dose of all three active ingredients comprised between 50 and 600 g, preferably between 100 and 500 µg.

For example, the formulations will be suitable for delivering 3-15 µg of formoterol (as fumarate dihydrate) per actuation, advantageously 5.5-6.5 µg or 10-13 µg per actuation, preferably 6 or 0.12 µg per actuation; 25-250 µg of beclometasone dipropionate (BDP) per actuation, advantageously 40-60 µg per actuation, or 80-120 µg per actuation, or 160-240 µg per actuation; and 5-65 µg of glycopyrronium (as bromide), advantageously 5-15 µg per actuation or 20-30 µg per actuation, preferably 12.5 µg or 25 µg.

In a particular embodiment, the formulation is suitable for delivering 6 µg of formoterol (as fumarate dihydrate) per actuation, 100 µg of beclometasone dipropionate, and 12.5 µg of glycopyrronium (as bromide) per actuation.

In another embodiment, the formulation is suitable for delivering 12 µg of formoterol (as fumarate dihydrate) per actuation, 200 g of beclometasone dipropionate, and 25 µg of glycopyrronium (as bromide) per actuation.

The dry powder formulation of the present invention may be utilized with any dry powder inhaler.

Dry powder inhaler (DPIs) can be divided into two basic types:

i) single dose inhalers, for the administration of single subdivided doses of the active compound; each single dose is usually filled in a capsule; and ii) multidose inhalers pre-loaded with quantities of active principles sufficient for longer treatment cycles.

The dry powder formulations of the present invention may be utilized with both multidose DPIs comprising a reservoir from which individual therapeutic dosages can be withdrawn on demand through actuation of the device, or with single dose inhalers.

Typical multidose devices that may be used are, for instance, Diskus™ of GlaxoSmithKhine, Turbohaler™ of AstraZeneca, Twisthaler™ of Schering, Clickhaler™ of Innovata, Spiromax™ of Teva, Novolizer™ of Meda, and Genuair™ of Almirall.

Examples of marketed single dose devices include Rotohaler™ of GlaxoSmithKline, Handihaler™ of Boehringer Ingelheim, and Breezehaler™ of Novartis.

Preferably, the powder formulation according to the invention is filled in a high-performing multidose DPI selected from the group consisting of NEXTHaler™, and its variant disclosed in the application no. PCT/EP2015/063803, which is incorporated herewith by reference in its entirety.

Other suitable high-performing multidose DPI are Novolizer™, and Genuair™.

To protect the DPIs from ingress of moisture into the formulation, it may be desirable to overwrap the device in a flexible package capable of resisting moisture ingress such as that disclosed in EP 1 760 008, which is incorporated herein by reference in its entirety.

Administration of the formulation prepared according to the process of the present invention is indicated for the prevention and/or treatment of chronic obstructive pulmonary disease (COPD) and asthma of all types and severity.

The formulation prepared according to the process of the present invention is also indicated for the prevention and/or treatment of further respiratory disorders characterized by obstruction of the peripheral airways as a result of inflammation and presence of mucus such as chronic obstructive bronchiolitis.

In certain embodiments, said formulation is particularly suitable for the prevention and/or treatment of severe and/or very severe forms COPD, and in particular for the maintenance treatment of COPD patients with symptoms, airflow limitation and history of exacerbations.

Furthermore, it might be suitable for the prevention and/or treatment of persistent asthma and asthma in patients not controlled with medium or high doses of ICS in combination with LABAs.

Other features of the invention will become apparent in the course of the following descriptions of exemplary embodiments which are given for illustration of the invention and are not intended to be limiting thereof.

EXAMPLES

Example 1. Preparation of the Carrier

Micronized alpha-lactose monohydrate (DFE Pharma, Germany) having the following particle size: d(v0.1)=1.5 micron; d(v0.5)=3.6 micron; and d(v0.9)=7.5 micron was utilized.

About 1694 g of said micronized alpha-lactose monohydrate, about 69.2 g of magnesium stearate (Peter Greven, Germany) and about 31.13 kg of fissured coarse particles of α-lactose monohydrate having a mass diameter of 212-355 micron (ratio 90:were fed into the vessel of a Turbula™ mixer (Willy A, Bachofen AG, Germany) and mixed. The mixing was carried out for 240 minutes at a speed of rotation of 16 r.p.m.

Example 2. Preparation of the Dry Powder Formulation

Micronized formoterol fumarate dihydrate (FF) having the following particle size was used: d(v0.1)=0.9 micron; d(v0.5)=2.3 micron; and d(v0.9)=4.2 micron.

Beclometasone dipropionate (BDP) having the following particle size was used: d(v0.1)=0.7 micron; d(v0.5)=1.5 micron; and d(v0.9)=2.8 micron.

Glycopyrronium bromide (GB) having the following particle size was used: d(v0.1)=0.4 micron; d(v0.5) 2.1 micron; d(v0.9)=5.5 micron.

The carrier as obtained in Example 1 was mixed in a dyna-MIX™ mixer with formoterol fumarate dihydrate, glycopyrronium bromide, and BDP at a speed of rotation of 24 and 28 r.p.m. alternatively for the two rotation axes for a time of 80 minutes.

Then 1694 g of micronised alpha-lactose monohydrate were added and mixed at a speed of rotation between 16 and 32 r.p.m, alternatively for the two rotation axes for a time of 150 minutes.

The resulting mixture was poured into a sieving machine available from Frewitt (Fribourg, Switzerland) equipped with a 600 micron mesh size sieve.

Upon sieving, the blend was finally mixed in a in the Dynamix mixer for 60 minutes at a rotation speed of 24 and 32 r.p.m alternately to achieve an homogeneous distribution of the active ingredients.

The ratio of the active ingredients to 10 mg of the carrier is 6 microg (μg) of FF dihydrate (theoretical delivered dose 4.5 μg), 100 microg (μg) of BDP and 12.5 microg (μg) of glycopyrronium bromide (theoretical delivered dose 10.0 μg).

The powder formulation was characterized in terms of the uniformity of distribution of the active ingredients and aerosol performances after loading it in the multidose dry powder inhaler described in WO 2004/012801, which is incorporated herein by reference in its entirety.

The uniformity of distribution of the active ingredients was evaluated by withdrawing 10 samples from different parts of the blend and evaluated by HPLC The results (mean value±RSD) are reported in Table 1.

The evaluation of the aerosol performance was carried out using the Next Generation Impactor (NGI) according to the conditions reported in the European Pharmacopeia 8.5th Ed 2015, par 2.9.18, pages 309-320, which is incorporated herein by reference in its entirety. After aerosolization of 3 doses from the inhaler device, the NGI apparatus was disassembled and the amounts of drug deposited in the stages were recovered by washing with a solvent mixture and then quantified by High-Performance Liquid Chromatography (HPLC).

The following parameters, were calculated: i) the delivered dose which is the amount of drug delivered from the device recovered in the all parts of impactor; ii) the fine particle mass (FPM) which is the amount of delivered dose having a particle size equal to or lower than 5.0 micron; iii) the extrafine FPM which is the amount of delivered dose having a particle size equal to or lower than 2.0 micron and/or equal to or lower than 1.0 micron and; iv) the mid FPM which is the amount of delivered dose having a particle size comprised between 2.0 and 5.0 micron v) the fine particle fraction (FPF) which is the ratio between the fine particle mass and the delivered dose: and vi) the MMAD.

The results (mean value±S.D) are reported in Table 1.

TABLE 1

| | Active ingredient |
|---|---|
| | FF |
| Uniformity of distribution | 100.5 (±1.5) |
| Delivered Dose [μg] | 5.1 |
| Fine Particle Mass [μg] | 2.9 |
| Fine Particle Fraction [%] | 54.8 |
| Mid Fine Particle Mass μ | 1.24 |
| Extrafine Particle Mass <2 μm [μg] | 1.7 |
| Extrafine Particle Mass <1 μm [μg] | 0.6 |
| Mid Fine particle Fraction [%] | 24.1 |
| Extrafine Particle Fraction <2 μm [%] | 32.5 |
| Extrafine Particle Fraction <1 μm [%] | 11.7 |
| MMAD [μm] | 1.9 |
| | GB |
| Uniformity of distribution | 101.4 (±1.6) |
| Delivered Dose [μg] | 11.1 |
| Fine Particle Mass [μg] | 5.4 |
| Fine Particle Fraction [%] | 48.1 |
| Mid Fine Particle Mass [μg] | 2.4 |
| Extrafine Particle Mass <2 μm [μg] | 2.9 |
| Extrafine Particle Mass <1 μm [μg] | 1.1 |
| Mid Fine particle Fraction [%] | 21.6 |
| Extrafine Particle Fraction <2 μm [%] | 26.4 |
| Extrafine Particle Fraction <1 μm [%] | 9.8 |
| MMAD [μm] | 1.9 |
| | BDP |
| Uniformity of distribution | 100.5 (±1.8) |
| Delivered Dose [μg] | 88.5 |
| Fine Particle Mass [μg] | 43.6 |
| Fine Particle Fraction [%] | 49.3 |
| Mid Fine Particle Mass [μg] | 15.2 |
| Extrafine Particle Mass <2 μm [μg] | 28.5 |
| Extrafine Particle Mass <1 μm [μg] | 12.4 |
| Mid Fine particle Fraction [%] | 17.1 |
| Extrafine Particle Fraction <2 μm [%] | 32.1 |
| Extrafine Particle Fraction <1 μm [%] | 13.9 |
| MMAD [μm] | 1.6 |

Example 3. Reference Example from WO 2015004243

Two powder formulations according to the teaching of Example 1, 3, 4 and 5 of WO 2015/004243, which is incorporated herein by reference in its entirety were prepared.

Their aerosol performances, evaluated as reported in Example 2 of the present application, are reported in Table 2. MF is for mechano-fusion apparatus and CY is for Cyclomix™ apparatus.

TABLE 2

| | Batch CY | Batch MF |
|---|---|---|
| FF | | |
| Delivered Dose [μg] | 5.3 | 5.8 |
| Fine Particle Mass [μg] | 4.0 | 4.3 |
| Fine Particle Fraction [%] | 75.9 | 73.4 |
| Extrafine Particle Mass Fraction <2 μm [μg] | 3.1 | 3.2 |

TABLE 2-continued

|  | Batch CY | Batch MF |
|---|---|---|
| Mid Fine Particle Mass [µg] | 1.0 | 1.1 |
| Extrafine Fine Particle Fraction <2 µm [%] | 57.1 | 55.2 |
| Mid Fine Particle Fraction [%] | 18.8 | 18.2 |
| MMAD [µm] | 1.1 | 1.2 |
| GB | | |
| Delivered Dose [µg] | 11.6 | 11.9 |
| Fine Particle Mass [µg] | 6.6 | 6.4 |
| Fine Particle Fraction [%] | 57.2 | 53.8 |
| Extrafine Particle Mass <2 µm [µg] | 4.0 | 4.0 |
| Mid Fine Particle Mass [µg] | 2.6 | 2.5 |
| Extrafine Particle Fraction <2 µm [%] | 34.9 | 33.2 |
| Mid Fine Particle Fraction [%] | 22.3 | 20.6 |
| MMAD [µm] | 1.8 | 1.4 |
| BDP | | |
| Delivered Dose [µg] | 90.6 | 95.7 |
| Fine Particle Mass [µg] | 64.5 | 66.9 |
| Fine Particle Fraction [%] | 71.2 | 69.9 |
| Extrafine Particle Mass <2 µm [µg] | 48.8 | 50.0 |
| Mid Fine Particle Mass [µg] | 15.7 | 16.9 |
| Extrafine Particle Fraction <2 µm [%] | 53.9 | 52.3 |
| Mid Fine Particle Fraction [%] | 17.3 | 17.6 |
| MMAD [µm] | 1.1 | 1.1 |

Example 4, Reference Example from WO 201/076843

A pMDI HFA solution formulation according to the teaching of WO 2011/076843 was prepared. Its aerosol performances, evaluated as reported in Example 2 of the present application, are reported in Table 3.

TABLE 3

| FF | |
|---|---|
| Delivered Dose [µg] | 5.0 |
| Fine Particle Mass [µg] | 2.3 |
| Fine Particle Fraction [%] | 45.7 |
| Extrafine Particle Mass Fraction <2 µm [µg] | 2.0 |
| Mid Fine Particle Mass [µg] | 0.3 |
| Extrafine Fine Particle Fraction <2 µm [%] | 45.7 |
| Mid Fine Particle Fraction [%] | 5.1 |
| MMAD [µm] | 1.0 |
| GB | |
| Delivered Dose [µg] | 10.6 |
| Fine Particle Mass [µg] | 4.8 |
| Fine Particle Fraction [%] | 45.1 |
| Extrafine Particle Mass <2 µm [µg] | 4.2 |
| Mid Fine Particle Mass [µg] | 0.5 |
| Extrafine Particle Fraction <2 µm [%] | 40.2 |
| Mid Fine Particle Fraction [%] | 5.0 |
| MMAD [µm] | 1.0 |
| BDP | |
| Delivered Dose [µg] | 87.8 |
| Fine Particle Mass [µg] | 40.4 |
| Fine Particle Fraction [%] | 46.0 |
| Extrafine Particle Mass <2 µm [µg] | 35.9 |
| Mid Fine Particle Mass [µg] | 4.5 |
| Extrafine Particle Fraction <2 µm [%] | 40.9 |
| Mid Fine Particle Fraction [%] | 5.2 |
| MMAD [µm] | 1.0 |

Example 5. Comparison of the FF/GB/BDP Dry Powder Formulation of the Invention with the Corresponding pMDI Solution Formulation of WO 2011/076843

The study is designed to show that the 6/100/12.5 µg FF/GB/BDP dry powder formulation of the present invention delivered through the DPI device disclosed in WO 2004/012801, which is incorporated herein by reference, is therapeutically equivalent to the corresponding pMDI HFA solution formulation of reference Example 4 in healthy volunteers. The pMDI formulation is delivered with and without the Aerochamber Plus™ Flow-Vu antistatic valved holding chamber.

Study Design:

Two parallel cohorts, open-label, randomized, 5-way crossover design.

Treatment: 8 single dose inhalations for a total dose of 48 microgram FF, 100 microgram GB, and 800 microgram BDP.

In order to obtain 20 evaluable subjects, approximately 25 healthy volunteers will be randomized.

The study consists of 2 parallel subject cohorts, of five treatment periods each, with single-dose administration, separated by 16±2 wash-out days between two consecutive treatment intakes.

Primary Objectives:

(1) To evaluate the total systemic exposure of 17-BMP (active metabolite of BDP), FF, and GB as $AUC_{0-4}$ and $C_{max}$; and (2) To evaluate the lung availability of 17-BMP (active metabolite of BDP), FF, and GB, assessed as systemic exposure ($AUC_{0-1}$ and $C_{max}$) upon gastrointestinal charcoal blockage, Secondary Objectives:

(1) To evaluate the pharamackinetic profile of BDP and additional PK parameters of 17-BMP, FF and GB assessed upon gastrointestinal charcoal blockage after administration: and (2) To evaluate the general safety and tolerability profile with and without activated charcoal.

Endpoints:

Primary PK variables

17-BMP/FF/GB: $AUC_1$a Co.

Secondary PK variables

17-BMP/FF/GB: $AUC_{0-\infty}$, $AUC_{0-30\ min}$, $t_{max}$ and $t_{1/2}$.

BDP: $AUC_{0-1}$, $C_{max}$ and $t_{max}$

Safety Variables

Adverse events and Adverse drug reactions.

Systolic Blood Pressure, Diastolic Blood Pressure, Heart Rate.

Measurements and Recording:

Pharmacokinetics Measures

BDP/17-BMP: 10 blood samples will be taken at the following time points: pre-dose (within 60 min from dosing), 10, 15 and 30 min, 1, 2, 4, 8, 12 and 24 hours post-dose.

FF: 10 blood samples will be taken at the following time points: pre-dose (within 60 min from dosing), 10, 15 and 30 min, 1, 2, 4, 8, 12 and 24 hours post-dose.

GB: 13 blood samples will be taken at the following time points: pre-dose (within 60 min from dosing), 10, 15 and 30 min, 1, 2, 4, 8, 12, 24, 32, 48 and 72 hours post-dose.

Safety Measures

Blood Pressure and local safety ECG: recording will be done

At screening to evaluate subject inclusion.
At each Period to evaluate subject safety, at the following time points: pre-dose (within 60 min from dosing), 10 min, 1 and 72h post-dose.
Clinical chemistry and serology; 1 blood sample will be taken at screening (fasting condition from at least 10 hours).
Hematology: 1 blood sample will be taken at screening (fasting condition from at least 11 hours).
Serum pregnancy test (only for women of childbearing potential) will be done at screening to evaluate subject inclusion.
Urine testing; urine samples will be taken for urinalysis, drug panel and cotinine test, at screening,
Urine pregnancy test (only for women of childbearing potential) will be done at each Period to evaluate subject inclusion (at randomization only) and subject safety Statistical Methods:
Primary PK Variables
17-BMP, FF and GB $C_{max}$ and $AUC_{0-4}$ (with/without activated charcoal) will be log-transformed and analysed using a linear model including treatment, sequence, period and subject within sequence as fixed effects. For all the foreseen comparisons, the ratios of adjusted geometric means will be calculated with their 90% two-sided confidence intervals (CIs).

Secondary PK Variables
17-BMP, FF and GB $AUC_{0-1}$, $AUC_{0-30\ min}$, and $t_{1/2}$ (with/without activated charcoal), BDP $C_{max}$ and $AUC_{0-1}$ (with/without activated charcoal) will be log-transformed and analysed using a linear model including treatment, sequence, period and subject within sequence as fixed effects. For all the foreseen comparisons, the ratios of adjusted geometric means will be calculated with their 90% two-sided confidence intervals (CIs).
17-BMP, BDP, FF and GB $t_{max}$ (with/without activated charcoal) will be analysed using the Wilcoxon signed rank test on untransformed data and the Hodges-Lehmann nonparametric estimate of location shift for all the foreseen comparisons.

Safety Variables
The number and the percentage of subjects who experience at least one TEAE, drug-related TEAL serious TEAE, severe TEAE, TEAE leading to study drug discontinuation and TEAE leading to death, as well as the number of events, will be summarized by treatment and overall.
The mean absolute value and the mean change from pre-dose (on the same day in each treatment period) to each post-dose time-point in Blood Pressure and Heart Rate will be calculated with their 95% CIs by treatment.
Where a numerical limit or range is stated herein, the endpoints are included. Also, all values and subranges within a numerical limit or range are specifically included as if explicitly written out.
As used herein the words "a" and "an" and the like carry the meaning of "one or more."
Obviously, numerous modifications and variations of the present invention are possible in light of the above teachings. It is therefore to be understood that, within the scope of the appended claims, the invention may be practiced otherwise than as specifically described herein.
All patents and other references mentioned above are incorporated in full herein by this reference, the same as if set forth at length.

The invention claimed is:

1. A process for preparing a powder formulation for inhalation for use in a dry powder inhaler, said powder comprising:
(A) a carrier, comprising:
(a) 80 to 95 percent by weight, based on the total weight of said carrier, of coarse particles of a physiologically acceptable excipient having a mean particle size of at least 175 µm; and
(b) 19.6 to 4.9 percent by weight, based on the total weight of said carrier, of micronized particles of a physiologically acceptable excipient, and 0.1 to 0.4 percent by weight, based on the total weight of said carrier, of a salt of a fatty acid; and
(B) micronized particles of an anti-muscarinic drug, a long-acting $\beta_2$-agonist, and optionally, an inhaled corticosteroid, as active ingredients, wherein said anti-muscarinic drug comprises glycopyrronium bromide, and said long-acting $\beta_2$-agonist comprises formoterol fumarate dihydrate,
said process comprising:
(i) mixing all of said coarse particles of a physiologically acceptable excipient; all of said salt of a fatty acid; a first portion of said micronized particles of a physiologically acceptable excipient; and all of said micronized particles of said long-acting $\beta_2$-agonist, said anti-muscarinic drug, and, optionally, said inhaled corticosteroid in a vessel of a shaker mixer at a speed of rotation not lower than 16 rpm for a time of not less than 60 minutes, to obtain a first mixture; and
(ii) adding the remaining part of said micronized particles of a physiologically acceptable excipient to said first mixture, to obtain a second mixture, and mixing said second mixture at a speed of rotation not lower than 16 rpm for a time of at least 120 minutes, to obtain said formulation,
wherein the extrafine particle fraction of each active ingredient is from 20 to 35%.

2. The process according to claim 1, further comprising:
(iii) further mixing said formulation obtained in (ii) to achieve a homogeneous distribution of said active ingredients.

3. The process according to claim 1, wherein said first portion of said micronized particles of a physiologically acceptable excipient is 40% to 60% by weight, based on the total weight of al of said micronized particles of a physiologically acceptable excipient.

4. The process according to claim 1, wherein said long-acting $\beta_2$-agonist further comprises at least one selected from the group consisting of formoterol, salmeterol, indacaterol, olodaterol, and vilanterol.

5. The process according to claim 1, wherein said anti-muscarinic drug further comprises at least one selected from the group consisting of glycopyrronium chloride, tiotropium bromide, umeclidinium bromide, and aclidinium bromide.

6. The process according to claim 1, wherein said inhaled corticosteroid is selected from the group consisting of beclomethasone dipropionate, beclomethasone dipropionate monohydrate, budesonide, fluticasone propionate, fluticasone furoate, and mometasone furoate.

7. The process according to claim 1, wherein said inhaled corticosteroid is beclometasone dipropionate.

8. The process according to claim 1, wherein said salt of a fatty acid is selected from the group consisting of magnesium stearate, sodium stearyl fumarate, sodium stearyl lactylate, sodium lauryl sulfate, and magnesium lauryl sulfate.

9. The process according to claim 8, wherein said salt of a fatty acid is magnesium stearate.

10. A powder formulation for inhalation for use in a dry powder inhaler, said powder comprising:
(A) a carrier, comprising:
  (a) 80 to 95 percent by weight, based on the total weight of said carrier, of coarse particles of a physiologically acceptable excipient having a mean particle size of at least 175 μm; and
  (b) 19.6 to 4.9 percent by weight, based on the total weight of said carrier, of micronized particles of a physiologically acceptable excipient, and 0.1 to 0.4 percent by weight, based on the total weight of said carrier, of magnesium stearate; and
(B) micronized particles of glycopyrronium bromide, beclometasone dipropionate, and formoterol fumarate dihydrate, as active ingredients,
wherein said formulation is obtainable by a process comprising:
(i) mixing all of said coarse particles of a physiologically acceptable excipient; all of said magnesium stearate; a first portion of said micronized particles of a physiologically acceptable excipient; and all of said micronized particles of glycopyrronium bromide, beclometasone dipropionate, and formoterol fumarate dihydrate in a vessel of a shaker mixer at a speed of rotation not lower than 16 rpm for a time of not less than 60 minutes, to obtain a first mixture; and
(ii) adding the remaining part of said micronized particles of a physiologically acceptable excipient to said first mixture, to obtain a second mixture, and mixing said second mixture at a speed of rotation not lower than 16 for a time of at least 120 minutes, to obtain said formulation,
wherein the extrafine particle fraction of each active ingredient is from 20 to 35%.

11. The powder formulation according to claim 10, wherein said process further comprises:
(iii) further mixing said formulation obtained in (ii) to achieve an homogeneous distribution of the active ingredients.

12. The powder formulation according to claim 10, wherein said first portion of said micronized particles of a physiologically acceptable excipient is 40% to 60% by weight, based on the total weight of all of said micronized particles of a physiologically acceptable excipient.

13. The powder formulation according to claim 10, whereby said extrafine particle fraction of beclometasone dipropionate, and formoterol fumarate dihydrate is from 20 to 35%, and said extrafine particle fraction of glycopyrronium bromide is from 20 to 30%.

14. The powder formulation according to claim 10, wherein said physiologically acceptable excipient is alpha-lactose monohydrate.

15. The powder formulation according to claim 10, wherein the coarse particles have a mass diameter of 210 to 360 μm.

16. A dry powder inhaler device, containing a dry powder formulation according to claim 10.

17. A method for the treatment of an inflammatory and/or obstructive airways disease, comprising administering to a subject in need thereof an effective amount of a dry powder formulation according to claim 10.

18. The method according to claim 17, wherein said disease is asthma or chronic obstructive pulmonary disease (COPD).

* * * * *

UNITED STATES PATENT AND TRADEMARK OFFICE
CERTIFICATE OF CORRECTION

PATENT NO. : 10,966,991 B2
APPLICATION NO. : 16/987695
DATED : April 6, 2021
INVENTOR(S) : Cafiero et al.

It is certified that error appears in the above-identified patent and that said Letters Patent is hereby corrected as shown below:

In the Specification

In Column 6, Line 8, delete "an" and insert -- a --, therefor.

In Column 8, Line 3, delete "inits" and insert -- in its --, therefor.

In Column 10, Line 58, delete "sterate" and insert -- stearate --, therefor.

In Column 11, Line 9, delete "a" and insert -- al --, therefor.

In Column 11, Line 14, delete "cos ϑMgSt+$f_{lactose}$" and insert -- cos $ϑ_{MgSt}$ +$f_{lactose}$ --, therefor.

In Column 12, Line 61, delete "an" and insert -- a --, therefor.

In Column 16, Line 17, delete "GlaxoSmithKhine," and insert -- GlaxoSmithKline, --, therefor.

In Column 17, Line 36, delete "an" and insert -- a --, therefor.

In Column 20, Line 36, delete "pharamackinetic" and insert -- pharmacokinetic --, therefor.

In Column 20, Line 44, delete "$AUC_1$a Co." and insert -- $AUC_{0-t,}$ $C_{max.}$ --, therefor.

In Column 21, Line 22, delete "$AUC_{0-4}$" and insert -- $AUC_{0-t}$ --, therefor.

In Column 21, Line 30, delete "$AUC_{0-1,}$" and insert -- $AUC_{0-\infty}$, --, therefor.

In Column 21, Line 32, delete "$AUC_{0-1}$" and insert -- $AUC_{0-t}$, --, therefor.

Signed and Sealed this
Twenty-third Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,966,991 B2

In the Claims

In Column 22, Claim 3, Line 46, delete "al" and insert -- all --, therefor.

In Column 24, Claim 11, Line 6, delete "an" and insert -- a --, therefor.